United States Patent
Capuzzi et al.

(10) Patent No.: US 10,758,466 B2
(45) Date of Patent: *Sep. 1, 2020

(54) POWDER-BASED COSMETIC COMPOSITIONS CONTAINING PELARGONIC ACID ESTERS

(71) Applicant: Novamont S.p.A., Novara (IT)

(72) Inventors: Luigi Capuzzi, Novara (IT); Francesca Digioia, Barengo (IT); Vanessa Bramati, Lainate (IT); Federica Carlomagno, Saronno (IT); Alessandra Cominetti, Agnadello (IT)

(73) Assignee: NOVAMONT, S.P.A., Novara (IT)

( * ) Notice: Subject to any disclaimer, the term of this patent is extended or adjusted under 35 U.S.C. 154(b) by 13 days.

This patent is subject to a terminal disclaimer.

(21) Appl. No.: 15/758,053

(22) PCT Filed: Sep. 7, 2016

(86) PCT No.: PCT/EP2016/071100
§ 371 (c)(1),
(2) Date: Mar. 7, 2018

(87) PCT Pub. No.: WO2017/042225
PCT Pub. Date: Mar. 16, 2017

(65) Prior Publication Data
US 2018/0256463 A1    Sep. 13, 2018

(30) Foreign Application Priority Data

Sep. 8, 2015  (IT) .................. 102015000049579

(51) Int. Cl.
*A61K 8/37* (2006.01)
*A61Q 1/12* (2006.01)
*A61K 8/02* (2006.01)

(52) U.S. Cl.
CPC .............. *A61K 8/37* (2013.01); *A61K 8/022* (2013.01); *A61Q 1/12* (2013.01); *A61K 2800/31* (2013.01)

(58) Field of Classification Search
CPC ...... A61K 2800/10; A61K 8/37; A61K 8/022; A61K 2800/31; A61Q 19/00; A61Q 1/00; A61Q 1/10; A61Q 1/12; A61Q 1/02; A61Q 17/04; A61Q 5/00; A61Q 19/10; A61Q 19/08
See application file for complete search history.

(56) References Cited

U.S. PATENT DOCUMENTS

| | | | | |
|---|---|---|---|---|
| 5,254,331 | A * | 10/1993 | Mausner | A61K 8/44 424/401 |
| 5,635,165 | A * | 6/1997 | Panitch | A61K 8/042 424/400 |
| 6,399,081 | B1 * | 6/2002 | Nakanishi | A61K 8/895 424/401 |
| 2004/0126350 | A1 | 7/2004 | Blin et al. | |
| 2015/0209429 | A9 | 7/2015 | Lathrop et al. | |

OTHER PUBLICATIONS

Namazi et al (Scientia Iranica, 2011, vol. 18, pp. 439-445) (Year: 2011).*
Johnson Jr et al (International Journal of Toxicology, 2011, pp. 228S-269S) (Year: 2011).*
"Sunscreen SPF 50+", GNPD, Mintel; Oct. 31, 2012; XP-002753099.
"Bb. Shine On (and On . . . ) Finishing Spray", GNPD, Mintel; Jun. 30, 2011; XP-002753100.
"Chic Minerals Loose Translucent Facial Powder", GNPD, Mintel; Nov. 30, 2012; XP-002762970.
"Harmony Eyes", GNPD, Mintel; Feb. 28, 2005; XP-002762971.
"Terracotta Makeup Collection", GNPD, Mintel; Aug. 31, 1999; XP-002762972.

* cited by examiner

Primary Examiner — Mark V Stevens
(74) Attorney, Agent, or Firm — Polsinelli PC

(57) ABSTRACT

Cosmetic composition comprising at least 35% by weight of a powder component and a binding component characterized in that it comprises at least one ester selected from neopentylglycol dipelargonate, glycerol tripelargonate, pentaerythritol tetrapelargonate and mixtures thereof.

22 Claims, No Drawings

POWDER-BASED COSMETIC COMPOSITIONS CONTAINING PELARGONIC ACID ESTERS

CROSS REFERENCE TO RELATED APPLICATIONS

This application is a National Phase filing under 35 U.S.C. § 371 of PCT/EP2016/071100 filed on Sep. 7, 2016; and this application claims priority to Application No. 102015000049579 filed in Italy on Sep. 8, 2015 under 35 U.S.C. § 119. The entire contents of each application are hereby incorporated by reference.

This invention relates to cosmetic compositions containing at least one powder and one or more esters selected from neopentyl glycol dipelargonate, glycerol tripelargonate and pentaerythritol tetrapelargonate.

In the cosmetics sector increasing attention has been paid to the identification of new ingredients having a low environmental impact, of natural and renewable origin, and at the same time having excellent functional and sensory properties.

Powder-based cosmetic compositions in particular find use in make-up products such as face powders, foundations, blushers, opaque make-up, eye shadow and skincare products such as talcs and dusting powders. They may be in loose or compacted form and have a component having a binding action to powders, lubricants, softeners and moisturisers, which also helps to ensure their adhesion to the skin and the spreadability of the product.

It has now been observed that polyol esters such as neopentyl glycol, glycerol and pentaerythritol with pelargonic acid which can be obtained from renewable sources have flow, film-forming and binding properties to powders and are particularly suitable for use as ingredients of the binding component in powder-based compositions for cosmetic use, i.e. for the preparation of products intended for application to the outer surface of the human body (epidermis, lips and cutaneous annexes) in order exclusively or mainly to clean them, perfume them, modify their appearance, protect them, maintain them in a good condition or correct body odours.

The object of this invention is therefore a cosmetic composition comprising at least 35% by weight of a powder component and a binding component characterised in that it comprises at least one ester selected from neopentyl glycol dipelargonate, glycerol tripelargonate, pentaerythritol tetrapelargonate and their mixtures. The said cosmetic composition advantageously comprises more than 40% by weight, preferably more than 50% by weight and more preferably more than 60% of the said powder component.

In particular, neopentyl glycol dipelargonate forms a light film and has a dry effect, glycerol tripelargonate forms a light film having excellent spreadability, while pentaerythritol tetrapelargonate forms a richer film and has excellent properties for the dispersion of colouring agents and the compactness of powders.

Thanks to these various functional and sensory properties, when used in combination between them the said esters constitute a non-unctuous film and impart excellent spreadability on the product and appreciable comfort. Mixtures of two or more esters, selected from neopentyl glycol dipelargonate, glycerol tripelargonate and pentaerythritol tetrapelargonate can surprisingly constitute the entire binding component of a powder-based cosmetic product, replacing the oils and silicones commonly used.

A cosmetic composition comprising at least a powder and a binding component, characterised in that the said binding component comprises at least two esters selected from neopentyl glycol dipelargonate, glycerol tripelargonate or pentaerythritol tetrapelargonate is therefore also an object of this invention. Cosmetic compositions according to this aspect of the invention preferably comprising at least 35% by weight of the said powder component are preferred.

Other advantages deriving from the use of neopentyl glycol dipelargonate, glycerol tripelargonate and pentaerythritol tetrapelargonate as ingredients in powder-based cosmetic compositions, in addition to those described above, will be apparent to those skilled in the art from reading this application.

The cosmetic composition according to the invention preferably contains from 1 to 20% by weight, more preferably from 3 to 15% by weight of the said binding component. In particular the said binding component preferably comprises from 1 to 10% by weight of compositions in compacted powder form and from 1 to 5% by weight of compositions in the form of loose powders. When used individually, neopentyl glycol dipelargonate, glycerol tripelargonate and pentaerythritol tetrapelargonate are preferably present in quantities of or less than 90%, more preferably of or less than 60%, even more preferably of or less than 15% by weight with respect to the binding components. Surprisingly, when two or more of the said esters are used in combination together they advantageously constitute 100% of the binding component.

According to an advantageous aspect of the invention, the said esters are prepared from pelargonic acid from renewable sources, obtained for example by processes for the oxidative cleavage of vegetable oils, fatty acids and their derivatives, whether modified or not. Preferred examples of renewable sources of pelargonic acid are vegetable oils from sunflowers, brassicaceae or thistles (such as *Cynara cardunculus* and *Silybum marianum*). Particularly preferred sources of pelargonic acid are represented by vegetable oils having a high oleic or erucic acid content.

The said pelargonic acid is preferably obtained by oxidative cleavage processes in which inorganic and organic peroxides, peracids, nitric acid, permanganates, periodates, $O_2$, $O_3$ or their gaseous mixtures are used as oxidising agents.

Oxidative cleavage processes in which peroxides such as hydrogen peroxide and $O_2$ or mixtures containing $O_2$ are used as oxidising agents are preferred. Specific examples are the oxidative cleavage processes described in applications WO 94/10122, WO 07/039481, WO 2008/138892, WO 2011/080296, WO 2011/080297 or WO 2013/079849.

According to a preferred aspect of the invention, the said esters are prepared from high purity pelargonic acid, preferably more than 95%, more preferably more than 98%, and a polyol selected from neopentyl glycol, glycerol or pentaerythritol, through an esterification reaction which is advantageously carried out in the absence of catalyst.

The said esterification is advantageously carried out in the presence of a molar excess of pelargonic acid with respect to the moles of polyol, preferably of or greater than 30% and less than 70%, operating at temperatures typically between 180 and 240° C., preferably 200-210° C. The water forming during the esterification reaction is advantageously removed from the reaction environment, for example by applying a gradual reduction in pressure; at the end of the reaction the excess acid is removed, preferably by evaporation. The ester so obtained can advantageously undergo purification treatments according to processes known to those skilled in the art, for example using activated carbons and decolouring earths with a view to removing any colour, odour and residual acidity. Examples of decolouring earths which may be used, including in combination with activated carbons, are graded Grade F-118FF, Grade F76 (marketed by BASF), Minclear N100, Minclear E100 and Pansil 2 (marketed by Tolsa).

In comparison with esters obtained by the common esterification procedures catalysed by metals, for example tin, the esters obtained by operating in accordance with the procedure described above do not contain metal residues which might influence their organoleptic properties (e.g. colour, odour) and their stability, and the toxicological properties of the finished cosmetic products. They therefore have the particular advantage of a lesser inorganic material content and require simplified preliminary treatments for use in the cosmetic environment.

Cosmetic compositions according to the present invention whose binding component comprises at least one of neopentyl glycol dipelargonate and glycerol tripelargonate are preferred for their peculiar properties; among these, those comprising glycerol tripelargonate are more preferred.

The binding component of powder-based compositions according to this invention may, in addition to the abovementioned esters, comprise other binding agents of the oily or waxy type, which may be of natural and/or synthetic origin.

Binding agents of the oily type are typically selected from esters, ethers, amides, alcohols and hydrocarbons of natural and/or synthetic origin, silicone oils or their mixtures.

Possible examples of esters of natural origin are triglycerides of saturated or unsaturated fatty acids, such as for example triglycerides of C8 and C10 acids, or their mixtures such as for example those present in vegetable oils. Suitable vegetable oils are for example olive oil, sunflower oil, maize oil, soya oil, castor oil, apricot oil, avocado oil, almond oil, macadamia oil, jojoba oil or karite oil.

Esters of synthetic origin are for example esters of linear and branched carboxylic acids with monoalcohols, such as isononyl isononanoate, isopropyl myristate, 2-ethy hexyl palmitate, isodecyl neopentanoate, isostearyl neopentanoate, 2-octyldodecyl stearate, 2-octyldodecyl erucate or isostearyl isostearate, diisostearyl maleate, C12-15 alkyl benzoate; esters of C7-C10 chain fatty acids with fatty alcohols; hydroxylated esters, such as isostearyl lactate, octyl hydroxystearate, octyldodecyl hydroxystearate; esters of polyols, such as propylene glycol dioctanoate, neopentyl glycol diheptanoate or diethylene glycol diisononanoate and pentaerythrityl tetraisostearate.

One example of an ether is dicaprilyl ether. One example of an amide is dibutyl lauroyl glutamide.

Other examples of oils include fatty alcohols such as octyldodecanol, hexyldodecanol, isostearyl alcohol.

Hydrocarbon oils of natural origin are for example terpene hydrocarbons such as squalene and squalane; hydrocarbon oils of mineral or synthetic origin are for example liquid paraffin and its derivatives such as isoparaffins (e.g. isododecane, isohexadecane, polydecene hydrogenate) and cycloparaffins.

The silicone oils are synthetic compounds based on silicon; they may be volatile or non-volatile, linear or cyclic. Examples of silicone oils are polysiloxanes and their derivatives comprising for example alkyl, alkoxyl or phenyl groups; silicone oils typically used include the polydimethylsiloxanes (Dimethicone), Amodimethicone, Cyclomethicones such as Cyclopentasiloxane and Cyclohexasiloxane, Amino Bispropyl Dimethicone, Aminopropyl Dimethicone, Amodimethicone hydroxystearate, Behenoxy-Dimethicone, C30-45 Alkyl Dimethicone, C24-28 Alkyl Dimethicone, C30-45 Alkyl Methicone, Cetearyl Methicone, Cetyl Dimethicone, Dimethoxysilyl Ethylenediaminopropyl Dimethicone, Hexyl Methicone, Hydroxypropyldimethicone, Stearamidopropyl Dimethicone, Stearoxy Dimethicone, Stearyl Methicone, Stearyl Dimethicone and Vinyl Dimethicone.

Binding agents of the waxy type are lipophilic and are in solid or paste form at ambient temperature (25° C.) and atmospheric pressure. These too may be of plant, animal, mineral and/or synthetic origin.

Suitable waxes are the waxes typically used in cosmetic compositions, and may be of natural and/or synthetic origin. Examples of natural waxes are beeswax or cera alba, carnauba wax, candelilla wax, Japan wax, rice wax, waxes deriving from hydrogenated oils such as jojoba oil or sunflower or coconut oils, esters of long chain saturated fatty acids with long chain mono-alcohols or their glycerides, such as cetyl palmitate, cetyl stearate, palmitic and stearic triglycerides.

Examples of mineral or synthetic waxes are lignite wax, microcrystalline wax, paraffin, ozokerite, ceresin, synthetic beeswax, lanolin and their esters with polyethylene glycols, polyethylene waxes, fatty acid esters having a melting point above 25° C., cetyl esters, polyamides.

Silicone waxes such as alkyl or alkoxy dimethicones or poly(di)methylsiloxanes having a high molecular rate may also be used.

The binding agents preferably used in the powder-based compositions according to the invention are selected from hydrocarbons such as polydecene, esters such as octyldodecyl stearoyl stearate triglycerides such as the triglycerides of capric/caprylic acids, fluid silicones, lanolin derivatives or their mixtures.

Salts of fatty acids such as magnesium stearate, zinc stearate, calcium stearate, lithium or aluminium stearate, zinc myristate, calcium palmitate and their mixtures may also advantageously be used in compositions according to the invention in combination with the abovementioned binding agents.

The abovementioned binding component has the function of encouraging adhesion and compaction in a mould of the powder components, in which other texturising agents, colouring agents and possibly perfume and preservative systems are dispersed. The said powder components preferably comprise one or more of talc, mica, kaolin, silica, silica-coated mica and talc, titania, titania-coated mica and talc, starches, apatite, perlite, polymers such as for example nylon and polyethylene, copolymer microspheres, silicone resin microbeads, or their mixtures.

Additional powder components include, but are not limited to, inorganic powders such as gums, chalk, Fuller's earth, sericite, muscovite, phlogopite, synthetic mica, lepidolite, biotite, lithia mica, vermiculite, aluminum silicate, alkyl and/or trialkyl aryl ammonium smectites, chemically modified magnesium aluminum silicate, organically modified montmorillonite clay, hydrated aluminum silicate, fumed aluminum starch, octenyl succinate, barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, colloidal silicone dioxide, and boron nitride; organic powders such as polyamide resin powder (nylon powder), cyclodextrin, methyl polymethacrylate powder, copolymer powder of styrene and acrylic acid, benzoguanamine resin powder, poly(ethylene tetrafluoride) powder, and carboxyvinyl polymer, cellulose powder such as hydroxyethyl cellulose and sodium carboxymethyl cellulose, ethylene glycol monostearate; inorganic white pigments such as magnesium oxide.

According to a preferred aspect of the invention, the powder component comprises talc. Due to their peculiar sensorial and functional properties, small amounts of the esters of pelargonic acids of the present invention are in fact advantageously required to bind talc when compared to the amount of vegetable oil typically required as binder in powder-based cosmetic compositions. Furthermore, cosmetic compositions comprising talc and neopentyl glycol dipelargonate and/or pentaerythritol tetrapelargonate show a creamy touch which is comparable to that of compositions containing silicone fluids such as phenyl trimethicone as binder.

According to a preferred embodiment, this invention relates to a cosmetic composition comprising with respect to the weight of the cosmetic composition:
(a) from 35 to 99% by weight of a powder component,
(b) from 1 to 20% by weight, preferably from 3 to 15% by weight, of a binding component comprising at least one ester selected from neopentyl glycol dipelargonate, glycerol tripelargonate, pentaerythritol tetrapelargonate and their mixtures,
(c) from 0 to 30% by weight of one or more texturising agents,
(d) from 0 to 15% by weight, preferably from 2 to 10%, of one or more colouring agents,
(e) from 0 to 15% by weight, preferably from 1 to 15%, more preferably from 5 to 15% by weight of a salt of a fatty acid,
(f) from 0 to 2% by weight, preferably from 0.01 to 1%, of one or more preservatives.

Examples of texturising agents which may advantageously be used in the compositions in question are starches, modified starches with hydrophobic groups, polymers such as polyamides, polyurethanes and polyacrylates, in particular polymethyl methacrylates.

According to one aspect of the invention, the said binding component comprises a single ester selected from neopentyl glycol dipelargonate, glycerol tripelargonate, pentaerythritol tetrapelargonate.

In the case in which the said ester is neopentyl glycol dipelargonate, this advantageously comprises between 0.1 and 15% by weight, preferably between 0.1 and 10% by weight, with respect to the weight of the binding component.

In the case in which the said ester is glycerol tripelargonate, this advantageously comprises between 0.1 and 60% by weight with respect to the weight of the binding component.

In the case in which the said ester is pentaerythritol tetrapelargonate, this advantageously comprises between 0.1 and 90% by weight, preferably between 0.1 and 80% by weight with respect to the weight of the binding component.

According to a preferred aspect of the invention, the binding component comprises a mixture of at least two of the said esters. Advantageously the said binding component comprises between 0.1 and 100% by weight of a binary mixture selected from neopentyl glycol dipelargonate and glycerol tripelargonate, or neopentyl glycol dipelargonate and pentaerythritol tetrapelargonate, or glycerol tripelargonate and pentaerythritol tetrapelargonate, or a ternary mixture comprising neopentyl glycol dipelargonate, glycerol tripelargonate and pentaerythritol tetrapelargonate.

According to a preferred aspect the cosmetic composition according to the invention advantageously comprises one or more colouring agents or dyes, in a quantity of preferably between 0.1% and 35% by weight, more preferably of between 0.1 and 30% by weight, even more preferably between 0.1 and 20% by weight. The said colouring agents may be soluble or insoluble in water, soluble or insoluble in fats, mineral or organic, natural or synthetic, and have the function of colouring or opacifying the cosmetic composition. Examples of suitable colouring agents are pigments, lacquers or pearls, which may be used as such or after surface treatments intended for example to modify water-repellence or hydrophilic properties. The pigments include derivatives of metals of an inorganic nature, for example oxides of iron, cerium, chromium, titanium, zinc or zirconium, silicates (e.g. micas), sulfosilicates (e.g. ultramarine) and their combinations, and molecules of an organic nature, such as for example plant extracts. By the term "pearls" are meant special pigments capable of developing reflection and refraction phenomena with light, which may be iridescent or non-iridescent, either organic (such as guanine, CI 75170) or inorganic (such as bismuth oxychloride, CI 77163, or sericite, CI 77019).

Thanks for the properties of the pelargonic acid esters present in the binding component the cosmetic compositions have the particular advantage of assisting the dispersion of pigments, whose colour they may help to intensify.

The cosmetic composition according to the invention may advantageously comprise one or more sun filters, in quantities of preferably between 0.05% and 35% by weight, preferably between 0.1 and 25% with respect to the weight of the cosmetic composition.

Sun filters have the function of protecting skin and/or hair from UVA/UVB radiation. These include for example filters or physical screens with reflecting properties such as for example zinc oxide and titanium dioxide, either in the form of nanomaterials or having particles of larger size, silica, kaolin, iron and/or magnesium oxides, and chemical filters, typically organic molecules capable of absorbing and converting the energy of ultraviolet radiation such as cinnamates, benzoimidazoles, benzophenones, benzylidene camphorate, PABA and its derivatives, salicylates, anthranylates, dibenzoyl methanes, octocrylene, triazines such as octyltriazone, bis-ethylhexyloxyphenol methoxyphenyl triazine and diethyl hexyl butamido triazone, natural antioxidants such as vitamin C and vitamin E or synthetic vitamins, such as Tinogard TT, or their combinations.

Physical and chemical filters may be of natural origin (such as for example gamma orizanol) or synthetic, and be used alone or more advantageously in combination.

Specific examples of sun filters suitable for use in the compositions according to the invention are octyl-methoxycinnamate, 2-ethyl-hexyl-4-dimethylaminobenzoate, butyl-methoxy-dibenzoylmethane, octyl triazone, diethyl hexylbutamido triazone, ethyl hexyl salicylate, zinc oxide, titanium dioxide, or their combinations.

Thanks to the properties of the pelargonic acid esters present in the binding component the cosmetic compositions according to the invention have the particular advantage of ensuring excellent dispersion of sun filters, whose protection factor they may help to increase. Additionally, they have shown a higher solubilisation and dispersion rates when compared to some of the commonly used oily solvents/dispersants. They are therefore suitable for the preparation of make-up products having a protective and anti-aging action.

Particularly suitable for this purpose are compositions comprising pentaerythritol tetrapelargonate and glycerol tripelargonate or their mixtures, which are particularly emollient. More preferred are compositions comprising pentaerythritol tetrapelargonate.

The powder-based cosmetic compositions according to this invention may also contain other additives typically used in the cosmetics field, such as antioxidants and/or vitamins, sun filters for product protection, preservatives, pH modifiers, moisturisers, conditioners, chelating agents, flow modifiers, texturising agents, film-forming agents, silicones, perfumes, essential oils or active ingredients, in particular cosmetically and/or dermatologically active ingredients.

By the term "preservatives" according to the invention are meant natural or synthetic substances having the primary function of inhibiting the growth of microorganisms in the cosmetic composition. The list of permitted preservatives makes reference to Appendix V to EC Regulation 1223/2009. The maximum permitted percentages used, any limitations and methods of use may be found within the document. The most widely used preservatives include for example: benzoic acid, propionic acid, salicylic acid, sorbic acid and their salts, p-hydroxybenzoic acid, its salts and esters, dehydroacetic acid, potassium sorbate, phenoxyethanol, imidazolidinyl urea. In combination or as an alternative to the said preservatives the cosmetic compositions according to the invention may also contain other substances capable of contributing to inhibition of the growth of microorganisms such as for example honey, essential oils such as extracts of rosemary, *Melaleuca alternifolia* and thyme, and complexing agents such as EDTA.

Each additive may be present in a quantity from 0 to 35%, preferably from 0 to 20% by weight, more preferably from 0 to 10%, with respect to the total weight of the cosmetic composition.

The cosmetic compositions according to the invention may be prepared according to processes known to those skilled in the art in the cosmetics field. For example, powders (including pigments and texturising agents) are subjected to mixing cycles in suitable mills, preferably provided with cooling systems to ensure dispersion of the heat produced during grinding; the nature of mixing and grinding cycles will be suitably identified by those skilled in the art on the basis of the nature of the powders. The ingredients of the binding component containing liposoluble preservatives will be mixed and raised to melting point or a higher temperature (typically 5-10° C. above melting point) in the presence of ingredients in solid or semi-solid form, such as waxes and hydrogenated derivatives. Once the dimensions and level of homogeneity required for the powders are achieved the binding component is gradually added to the powders. The mixture so obtained then undergoes further mixing cycles to encourage incorporation of the binding components. Any pearlescent pigments may be added during this stage and undergo a further mixing cycle. The bound powder so obtained is discharged from the mill and sieved.

According to a preferred form of preparation the desired quantities of ingredients of the composition undergo one or more operations selected from grinding, sieving and pressing in a mould. Thanks to the properties of the esters neopentyl glycol dipelargonate, glycerol tripelargonate, pentaerythritol tetrapelargonate and their mixtures the powder-based cosmetic compositions which are the object of this invention are particularly pleasant to touch and at the same time are characterised by excellent spreading.

They therefore find application in make-up products such as compacted powders, face powders, foundations, blushers, opaque make-up and eye shadow.

One aspect of this invention relates to powder-based cosmetic compositions containing a binary mixture of neopentyl glycol dipelargonate and glycerol tripelargonate. The said cosmetic compositions provide a light film and good spreadability.

Another aspect of this invention relates to powder-based cosmetic compositions containing a binary mixture of neopentyl glycol dipelargonate and pentaerythritol tetrapelargonate. The said cosmetic compositions provide a light but comfortable film and have good spreadability.

Another aspect of this invention relates to powder-based cosmetic compositions containing a binary mixture of glycerol tripelargonate and pentaerythritol tetrapelargonate. The said cosmetic compositions have a more apparent and comfortable, non-unctuous, film and good spreadability.

Another aspect of this invention relates to powder-based cosmetic compositions containing a ternary mixture of neopentyl glycol dipelargonate, glycerol tripelargonate and pentaerythritol tetrapelargonate. The said cosmetic compositions have a very apparent and comfortable, non-unctuous, film, and excellent spreadability.

This invention will now be illustrated in detail by the following non-limiting examples.

EXAMPLES

The esters used in the following examples have been prepared using pelargonic acid originating from the oxidative cleavage of sunflower oil having a high oleic acid content. In particular pelargonic acid obtained according to the process described in patent application WO 2011080296 has been used at the end of stage c) of separation of the monocarboxylic acids from the triglycerides containing more than one acid function and subsequent rectification to remove the fraction comprising light monocarboxylic acids, such as described in Example 1. The pelargonic acid used has a purity of 99%.

Preparation of Neopentyl Glycol Dipelargonate, Glycerol Tripelargonate and Pentaerythritol Tetrapelargonate Esters The esterification reactions for synthesis of the three esters were carried out in the absence of catalyst and with a molar excess of pelargonic acid of 30% molar with respect to the polyol used (neopentyl glycol, glycerine or pentaerythritol). In order to favour the removal of esterification water the temperature of the acid/polyol mixtures was increased to 200-210° C. in the course of the reactions; once this temperature had been reached gradual vacuum was applied up to 100 mbar in order to favour conversion of the reagents. Once the reactions were complete, after a quantity of reaction water corresponding to the theoretical quantity had been obtained, the excess acid was recovered by evaporation, keeping the temperature around 180-200° C. with a vacuum of 5 to 10 mbar.

The products then underwent decolouring treatment with activated carbon and decolouring earth and neutralisation through the addition of a quantity of calcium hydroxide and water (in a 1:1 ratio by weight) of between 1 and 2% by weight with regard to each ester, heating to 60° C. with stiffing for 30 minutes. After water had been completely removed by heating to 80-100° C. in a vacuum, a filtering earth (Celite 512; 1% by weight with respect to the ester) was added with stirring, and the liquid was filtered under vacuum on a bed of the same earth, obtaining a clear product.

Measurements of acidity made in accordance with standard ASTM D664 showed a residual acidity of less than 0.1 mg KOH/g for each of the three esters.

Preparation of Cosmetic Compositions

The binding agents for the product were weighed and placed together with liposoluble preservatives in a melter of suitable capacity, provided with a heating jacket, within which they were mixed. In the presence of components in solid or semi-solid form having a binding action, such as waxes and hydrogenated derivatives, the mixture was heated with constant stirring to reach and exceed the melting point of the products of approximately 5-10° C.

All the powders (comprising texturising agents and pigments) were placed in a mill of suitable capacity, provided with a cooling system, and underwent mixing cycles established on the basis of the nature of the powders, with possible cooling in order to contain the rise in temperature deriving from mixing.

Once the powders undergoing mixing had been checked to be homogeneous, the previously prepared binding component was added gradually as a stream and further mixing was performed to enable it to be incorporated into the powders. When pearlescent pigments were present, these were added to the processing at this stage and subjected to a further mixing cycle.

At the end of the production process the bound powder was discharged from the mill and sieved.

Examples of cosmetic compositions according to the invention are shown in the tables below. The list of ingredients (in accordance with the INCI nomenclature) and the percentage composition by weight of each ingredient in relation to the total weight of the composition are indicated for each composition.

Examples 1 (Comparison)-5

Compacted Powder-Based Compositions (Bronzing Powder)

| INCI | Example 1 (comparison) | Example 2 | Example 3 | Example 4 | Example 5 |
|---|---|---|---|---|---|
| Talc | 81 | 81 | 81 | 81 | 81 |
| Octyldodecyl Stearoyl Stearate | 6 | 1 | — | 5 | — |
| Glycerol tripelargonate | — | 5 | 5 | — | — |
| Pentaerythritol tetrapelargonate | — | — | 2 | — | 2 |
| Neopentyl glycol dipelargonate | — | — | — | 1 | 5 |
| Magnesium Stearate | 3 | 3 | 3 | 3 | 3 |
| Ethylene/Acrylic Acid Copolymer | 2.5 | 2.5 | 1.5 | 2.5 | 1.5 |
| Sorbic Acid | 0.35 | 0.35 | 0.35 | 0.35 | 0.35 |
| Sodium Dehydroacetate | 0.35 | 0.35 | 0.35 | 0.35 | 0.35 |
| CI 77491 (Iron Oxides) | 2.1 | 2.1 | 2.1 | 2.1 | 2.1 |
| CI 77492 (Iron Oxides) | 3.4 | 3.4 | 3.4 | 3.4 | 3.4 |
| CI 77499 (Iron Oxides) | 0.6 | 0.6 | 0.6 | 0.6 | 0.6 |
| CI 77891 (Titanium Dioxide) | 0.7 | 0.7 | 0.7 | 0.7 | 0.7 |

The five compositions showed comparable sensorial properties. A can be seen from Examples 3 and 5, when used in combination between them the said esters can surprisingly constitute the entire binding component of a compacted powder-based composition, replacing the commonly used Octyldodecyl Stearoyl Stearate. They also can partly replace the Ethylene/Acrylic Acid Copolymer, with the same effect.

Examples 6 (Comparison)-10

Loose Powder-Based Compositions (Face Powder)

| INCI | Example 6 (comparison) | Example 7 | Example 8 | Example 9 | Example 10 |
|---|---|---|---|---|---|
| Talc | 83.94 | 83.94 | 83.94 | 83.94 | 83.94 |
| Triticum Vulgare Starch | 5.5 | 5.5 | 5.5 | 5.5 | 5.5 |
| Glycerol tripelargonate | — | — | 3.5 | — | 1.7 |
| Pentaerythritol tetrapelargonate | — | 3.5 | 0.5 | 2.2 | 0.5 |
| Neopentyl glycol dipelargonate | — | — | — | 1 | — |
| Zinc Stearate | 2 | 2 | 2 | 2 | 2 |
| Octyldodecanol | 1.8 | — | — | 1.8 | 1.8 |
| Caprylic/Capryc Triglyceride | 1.7 | — | — | — | — |
| Simmondsia Chinensis Seed Oil | 0.5 | 0.5 | — | — | — |
| Tocopherol | 0.1 | 0.1 | 0.1 | 0.1 | 0.1 |
| Glyceryl Caprylate | 1.5 | 1.5 | 1.5 | 1.5 | 1.5 |
| Sodium Dehydroacetate | 0.35 | 0.35 | 0.35 | 0.35 | 0.35 |
| CI 77491 (Iron Oxides) | 0.15 | 0.15 | 0.15 | 0.15 | 0.15 |
| CI 77492 (Iron Oxides) | 0.44 | 0.44 | 0.44 | 0.44 | 0.44 |
| CI 77499 (Iron Oxides) | 0.02 | 0.02 | 0.02 | 0.02 | 0.02 |
| CI 77891 (Titanium Dioxide) | 2 | 2 | 2 | 2 | 2 |

Example 11—Pigments Dispersion

Black Iron Oxide particles (CI77499, commercially available as YPC335200 from Yipin) were dispersed in each of the ester oils of the present invention and in ester oil commonly used as cosmetic ingredients. Each sample of powder particles was wetted by the dropwise addition of one ester oil and then vigorously blended using a spatula until the wet point and the flow point were reached.

The wet point is defined as the minimum volume of dispersant solution to produce a soft coherent mass; the further minimum addition of dispersant solution to produce flow or falling off of the homogeneous mass from the vertical blade of a horizontally held spatula determines the flow point.

The amounts of dispersant solution (i.e. ester oil) needed to reach the wet point (Wp) and the flow point (Fp) were recorded and reported in the table below, expressed in grams per 100 g of pigment.

| Pigment dispersion | Wp (g) | Fp (g) |
|---|---|---|
| Isononyl Isononanoate | 50.00 | 145.00 |
| Caprylic/Capric Triglyceride | 60.00 | 130.00 |
| C12-15 Alkyl Benzoate | 60.00 | 143.00 |
| Neopentyl glycol dipelargonate | 61.00 | 166.00 |
| Glycerol tripelargonate | 60.00 | 100.00 |
| Pentaerythritol tetrapelargonate | 62.00 | 132.00 |

The ester oils of the invention showed dispersion properties comparable to those of commonly used cosmetic ingredients. Surprisingly, glycerol tripelargonate has revealed a Fp significantly close to the Wp, demonstrating dispersion properties even better than those of Caprylic/Capric Triglyceride. This minimum difference results in a considerable advantage as it enables significant cost savings on the final composition (wherein about 30% less solvent is required).

The dispersions thus prepared were tested on the forearm to assess the differences in terms of smoothness, writing capabilities, color consistency, gloss effect. A scale from 1 (low) to 5 (high) was used. The sensory evaluation test results are reported in the table below.

| Sensory evaluation | Isononyl Isononanoate | Caprylic/Capric Triglyceride | C12-15 Alkyl Benzoate | Neopentyl glycol dipelargonate | Glycerol tripelargonate | Pentaerythritol tetrapelargonate |
|---|---|---|---|---|---|---|
| Flowability | 4 | 4 | 2 | 2 | 5 | 4 |
| Writing capability/color intensity | 2 | 4 | 4 | 3 | 4 | 4 |
| Film evenness | 2 | 3 | 4 | 4 | 4 | 4 |
| Gloss effect | 2 | 3 | 4 | 2 | 5 | 5 |

The pigment dispersions in glycerol tripelargonate and pentaerythritol tetrapelargonate showed flowability, film evenness and gloss effect higher than those prepared with commonly used ester oils.

Example 12—UV Filters Dispersion

The dispersibility of a solid UV filter in different ester oils was tested using Titania ($TiO_2$, commercially available as Titanio Biossido Anatasio from A.C.E.F.). Various ratios of solute/solvent (1% and 10% $TiO_2$) were prepared under stirring at 70° C. for 30 minutes. The dispersions were then observed after a storage period of 0 hours ($t_0$) and 24 hours ($t_{24}$) at ambient temperature (25° C.) to check for the formation of any sediment deposit. Results for each ester are shown in the table below (D=homogeneous dispersion; S=sediment deposit).

| Filters dispersion | $t_0$ | | $t_{24}$ | |
|---|---|---|---|---|
| | 1% | 10% | 1% | 10% |
| Isononyl Isononanoate | D | D | S | S |
| Caprylic/Capric Triglyceride | D | D | S | S |
| C12-15 Alkyl Benzoate | D | D | S | S |
| Neopentyl glycol dipelargonate | D | D | S/D | S/D |
| Glycerol tripelargonate | D | D | D | S/D |
| Pentaerythritol tetrapelargonate | D | D | D | D |

The dispersant capability of the pelargonic acid esters of the invention was equivalent to that of commonly used esters such as Isononyl Isononanoate, Caprylic/Capric Triglyceride and C12-15 Alkyl Benzoate.

Glycerol tripelargonate and pentaerythritol tetrapelargonate showed an even better dispersion of Titania compared with reference solvents.

Example 13—UV Filters Solubility

The solubility of the chemical UV filter Butyl methoxydibenzoylmethane (CAS N° 70356-09-1, commercially available as PARSOL® 1789 from DSM) in different ester oils was tested. Various ratios of solute/solvent (5%, 10%, 20% and 30% by weight; total amount filter+solvent: 10 g) were prepared in glass bottles in a water bath at 60° C. The solutions were then observed after a storage period of 2 hours at 20° C. to check for the formation of any sediment deposit. Once identified the solubility range, which ranged between 10-20% for each filter/solvent couple, the maximum concentration of soluble filter in each ester was determined by making repeated additions of lower amounts of the filter to the solutions at 10%, until the formation of precipitate was observed. Each addition was carried out at a temperature of 60° C. and followed by cooling. The solutions were allowed to stand at the constant temperature of 20° C. for two hours before checking for precipitation (by visual determination).

Results for each ester are shown in the table below:

| Filters solubility | % w/w, 20° C. |
|---|---|
| Caprylic/Capric Triglyceride | 14 |
| C12-15 Alkyl Benzoate | 14 |
| Neopentyl glycol dipelargonate | 18 |
| Glycerol tripelargonate | 18 |
| Pentaerythritol tetrapelargonate | 18 |

The solubility values of Butyl methoxydibenzoylmethane in the three pelargonic acid esters at 20° C. was equivalent and considerably higher than that in commonly used esters such as Caprylic/Capric Triglyceride and C12-15 Alkyl Benzoate.

Example 14—UV Filters Solubility

The solubility of the chemical UV filter Benzophenone-3 (CAS N° 131-57-7, commercially available as UVASORB® MET from 3V Sigma) in pentaerythritol tetrapelargonate and in a ternary mixture of neopentyl glycol dipelargonate, glycerol tripelargonate and pentaerythritol tetrapelargonate (in a weight ratio of 1:1:1) was determined at 20° C. as described in Example 13.

The solubility value of Benzophenone-3 in pentaerythritol tetrapelargonate was of 14% w/w at 20° C., while the corresponding solubility value of the same filter in the ternary mixture was of 19% w/w. The mixture of pelargonic acid esters according to the invention therefore revealed a surprisingly high ability to solubilize UV filters when compared to the one of the individual ester.

The invention claimed is:

1. A powder-based cosmetic composition comprising more than 40% by weight of a powder component and from 1 to 20% by weight of a binding component wherein the said binding component is at least one ester selected from neopentylglycol dipelargonate, glycerol tripelargonate, pentaerythritol tetrapelargonate and mixtures thereof.

2. The cosmetic composition according to claim 1 wherein the said binding component is at least two esters selected from neopentylglycol dipelargonate, glycerol tripelargonate, pentaerythritol tetrapelargonate or mixtures thereof.

3. The cosmetic composition according to claim 1 comprising from 3 to 15% by weight of the said binding component.

4. The cosmetic composition according to claim 1 further comprising an oily and/or waxy binding agent.

5. The cosmetic composition according to claim 4 wherein the said oily and/or waxy binding agent is selected from hydrocarbons, esters, triglycerides, fluids silicones, and lanolin derivatives.

6. The cosmetic composition according to claim 1 wherein the said powder component comprises one or more of talc, mica, kaolin, silica, silica-coated mica and talc, titania, titania-coated mica and talc, starches, apatite, perlite, polymers, copolymer microspheres, silicone resin microbeads, or their mixtures.

7. The cosmetic composition according to claim 1 comprising at least a sun filter.

8. The cosmetic composition according to claim 1 comprising, relative to the total weight of the cosmetic composition:
   a) up to 99% by weight of a powder component,
   c) from 0 to 30% by weight of one or more texturizing agents,
   d) from 0 to 15% by weight of one or more colouring agents,
   e) from 0 to 15% by weight of a fatty acid salt, and
   f) from 0 to 2% by weight of one or more preservatives.

9. The cosmetic composition according to claim 1, wherein the said binding component comprises from 0.1 to 15% by weight of neopentylglycol dipelargonate.

10. The cosmetic composition according to claim 1, wherein the said binding component comprises from 0.1 to 60% by weight of glycerol tripelargonate.

11. The cosmetic composition according to claim 1, wherein the said binding component comprises from 0.1 to 90% by weight of pentaerythritol tetrapelargonate.

12. The cosmetic composition according to claim 1, wherein the said binding component is a binary mixture selected from neopentylglycol dipelargonate and glycerol tripelargonate, or neopentylglycol dipelargonate and pentaerythritol tetrapelargonate, or glycerol tripelargonate and pentaerythritol tetrapelargonate, or a ternary mixture consisting of neopentylglycol dipelargonate, glycerol tripelargonate and pentaerythritol tetrapelargonate.

13. A method for the preparation of a product for make-up selected from loose powders, compact powders, face powders, foundations, blushers, and eyeshadows, wherein the method comprises including in said product a cosmetic composition according to claim 1.

14. The cosmetic composition according to claim 2 comprising from 3 to 15% by weight of the said binding component.

15. The cosmetic composition according to claim 2 further comprising an oily and/or waxy binding agent.

16. The cosmetic composition according to claim 3 further comprising an oily and/or waxy binding agent.

17. The cosmetic composition according to claim 2 wherein the said powder component comprise one or more of talc, mica, kaolin, silica, silica-coated mica and talc, titania, titania-coated mica and talc, starches, apatite, perlite, polymers, copolymer microspheres, silicone resin microbeads, or their mixtures.

18. The cosmetic composition according to claim 3 wherein the said powder component comprise one or more of talc, mica, kaolin, silica, silica-coated mica and talc, titania, titania-coated mica and talc, starches, apatite, perlite, polymers, copolymer microspheres, silicone resin microbeads, or their mixtures.

19. The cosmetic composition according to claim 4 wherein the said powder component comprise one or more of talc, mica, kaolin, silica, silica-coated mica and talc, titania, titania-coated mica and talc, starches, apatite, perlite, polymers, copolymer microspheres, silicone resin microbeads, or their mixtures.

20. The cosmetic composition according to claim 5 wherein the said powder component comprise one or more of talc, mica, kaolin, silica, silica-coated mica and talc, titania, titania-coated mica and talc, starches, apatite, perlite, polymers, copolymer microspheres, silicone resin microbeads, or their mixtures.

21. The cosmetic composition according to claim 1 comprising more than 50% by weight of the powder component.

22. The cosmetic composition according to claim 1 comprising more than 60% by weight of the powder component.

* * * * *